United States Patent [19]

Kumazawa et al.

[11] Patent Number: 4,863,505

[45] Date of Patent: Sep. 5, 1989

[54] NOVEL DERIVATIVE OF AZOLE, AND AGRICULTURAL AND HORTICULTURAL COMPOSITION CONTAINING THE SAME AS AN ACTIVE INCREDIENT

[75] Inventors: Satoru Kumazawa; Atsushi Ito; Nobuo Sato; Toshihide Saishoji; Masahiro Hamada; Shiro Yamazaki; Hiroyuki Enari, all of Iwaki, Japan

[73] Assignee: Kureha Kagaku Kogyo Kabushiki Kaisha, Tokyo, Japan

[21] Appl. No.: 903,992

[22] Filed: Sep. 4, 1986

[30] Foreign Application Priority Data

Sep. 12, 1985 [JP] Japan .................................. 60-202431
Jun. 25, 1986 [JP] Japan .................................. 61-147175

[51] Int. Cl.$^4$ .................. A01N 43/653; C07D 249/12
[52] U.S. Cl. ........................................... 71/92; 71/76; 548/262; 548/341; 514/383
[58] Field of Search ...................... 548/262; 71/76, 92; 514/383

[56] References Cited

U.S. PATENT DOCUMENTS 4,623,654 11/1986 Parry et al. ......................... 548/262
4,684,396 8/1987 Clough et al. ...................... 548/262

FOREIGN PATENT DOCUMENTS

| 0000950 | 3/1979 | European Pat. Off. . |
| 0040345 | 11/1981 | European Pat. Off. ............. 548/262 |
| 0052425 | 5/1982 | European Pat. Off. ............. 548/262 |
| 0502424 | 5/1982 | European Pat. Off. ............. 548/262 |
| 0094146 | 11/1983 | European Pat. Off. ............. 548/262 |
| 60-215674 | 9/1985 | Japan .................................. 548/262 |

OTHER PUBLICATIONS

Ullmanns Encyklopadie der technischen Chemie, 4 Auflage, Bd. 12, Seite 12.

*Primary Examiner*—Glennon H. Hollrah
*Assistant Examiner*—Patricia L. Morris
*Attorney, Agent, or Firm*—John P. White

[57] ABSTRACT

Disclosed herein are a derivative of azole having a usefulness in controlling plant fungal diseases, in regulating plant growth and in killing weeds, a process for producing the derivative of azole and a composition having a fungicidal activity, a plant growth regulating activity and a herbicidal activity and containing the derivative of azole as an active ingredient for use in agriculture and horticulture.

14 Claims, No Drawings

NOVEL DERIVATIVE OF AZOLE, AND AGRICULTURAL AND HORTICULTURAL COMPOSITION CONTAINING THE SAME AS AN ACTIVE INCREDIENT

BACKGROUND OF THE INVENTION

The present invention relates to a derivative of azole represented by the formula (I):

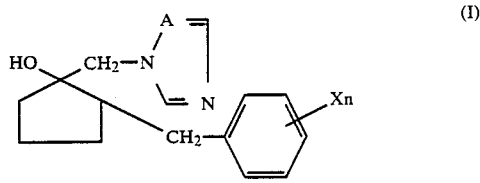

wherein X represents a hydrogen atom, a halogen atom, an alkyl group, a haloalkyl group, a phenyl group, a cyano group or a nitro group and X can be the same or different atom or group, n represents an integer of from 1 to 5 and A represents a nitrogen atom or a methine group, a process for producing the derivative of azole and an agricultural and horticultural composition having a fungicidal activity, a plant glowth regulating activity and a herbicidal activity and containing the derivative of azole as an active ingredient.

Field crops are badly damaged by plant diseases every year, and agricultural chemicals to control them cause the serious environmental pollution, which has become people's great concern. Therefore, there has been a great demand for a new fungicide for agriculture and horticulture which has a low level of toxicity to human, animals, birds and fish and also has a low level of phytotoxicity to useful plants. Such a fungicide should be highly safe in handling, have very little adverse effect on the environment, and produce outstanding control effect for a wide variety of plant diseases.

In an effort to develop such an epoch-making fungicide for agriculture and horticulture, the present inventors studied for new compounds instead of mere modifications of existing compounds. To this end, they synthesized a large number of derivatives of azole and tested their usefulness in practical use. As a result, it was found that derivatives of azole represented by the formula (I) have the above-mentioned characteristics.

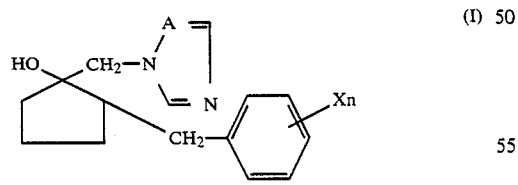

wherein X represents a hydrogen atom, a halogen atom, an alkyl group, a haloalkyl group, a phenyl group, a cyano group or a nitro group and X can be the same or different atom or group, n represents an integer of from 1 to 5 and A represents a nitrogen atom or a methine group.

In addition and surprisingly enough, the present inventors have found that the derivative of azole exert not only a fungicidal effect but also a plant growth control effect and herbicidal effect. These findings led to the present invention.

SUMMARY OF THE INVENTION

It is an object of the present invention to provide a novel derivative of azole represented by the formula (I).

It is another object of the present invention to provide a fungicide for agriculture and horticulture which is effective against a large variety of plant diseases with a low toxicity to human, animals, birds and fish and a low phytotoxicity to useful plants, the fungicide further exerting the plant growth control effect and herbicidal effect.

It is further object of the present invention to provide a composition for use in agriculture and horticulture containing as an active ingredient a derivative of azole represented by the formula (I), said chemical being superior in handling safety and environmental protection.

BRIEF EXPLANATION OF THE DRAWINGS

FIGS. from 1 to 36 attached hereto are the infrared absorption spectra of the derivative of azole pertaining to the present invention. The figure numbers correspond to the respective compound numbers shown in Table 1.

DETAILED DESCRIPTION OF THE INVENTION:

The feature of the present invention lies in; (1) a derivative of azole represented by the formula (I):

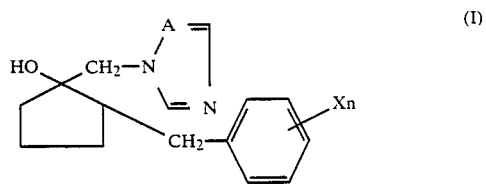

wherein X represents a hydrogen atom, a halogen atom, an alkyl group, a haloalkyl group, a phenyl group, a cyano group or a nitro group and X can be the same or different atom or group, n represents an integer of from 1 to 5 and A represents a nitrogen atom or a methine group, (2) a process for producing the derivative of azole by reacting a derivative of oxirane represented by the formula (II):

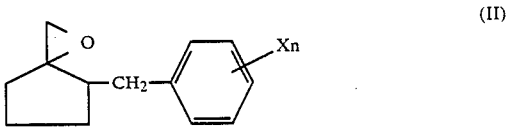

wherein X and n have the same meaning as in the formula (I), with 1,2,4-triazole or imidazole and (3) an agricultural and horticultural composition containing as an active ingredient a derivative of azole represented by the formula (I) and having a fungicidal activity, a plant growth controlling activity and a herbicidal activity.

A derivative of azole represented by the formula (I) is a novel compound and some of the derivatives are shown in Table 1 below with respective melting points.

A detailed description is given below of the process for producing a derivative of azole represented by the formula (I) and utilization of the derivative of azole as an agricultural and horticultural composition.

A derivative of azole represented by the formula (I) is produced by reacting a derivative of oxirane represented by the formula (II) with 1,2,4-triazole or imidazole represented by the formula (III) in the presence of a diluent:

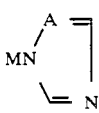
(III)

wherein M represents a hydrogen atom or an alkali metal and A represents a nitrogen atom or a methine group.

TABLE 1

| Number of compound | Indication in Formula (I) X | n | A | Position on phenyl radical in Formula (I) where X is | Melting point (°C.) |
|---|---|---|---|---|---|
| 1 | H | 1 | N | — | 140–141 |
| 2 | H | 1 | CH | — | 130–131 |
| 3 | Cl | 1 | N | 4, | 115–116 |
| 4 | Cl | 1 | CH | 4, | 115–116 |
| 5 | F | 1 | N | 4, | 135–136 |
| 6 | F | 1 | CH | 4, | 139–140 |
| 7 | Cl | 2 | N | 2,4, | 120–121 |
| 8 | Cl | 2 | CH | 2,4, | 150–151 |
| 9 | t-C4H9 | 1 | N | 4, | 129–130 |
| 10 | t-C4H9 | 1 | CH | 4, | 123–124 |
| 11 | C6H5 | 1 | N | 4, | 146–147 |
| 12 | C6H5 | 1 | CH | 4, | 182–183 |
| 13 | CF3 | 1 | N | 3, | 152–153 |
| 14 | CF3 | 1 | CH | 3, | 87–88 |
| 15 | Cl | 1 | N | 3, | 152–153 |
| 16 | Cl | 1 | CH | 3, | 105–106 |
| 17 | NO2 | 1 | N | 4, | 131–132 |
| 18 | F | 2 | N | 2,6, | 104–105 |
| 19 | F | 2 | CH | 2,6, | 150–151 |
| 20 | Br | 1 | N | 4, | 106–107 |
| 21 | Br | 1 | CH | 4, | 119–120 |
| 22 | Cl | 1 | N | 2, | 154–155 |
| 23 | Cl | 1 | CH | 2, | 103–104 |
| 24 | CH3 | 1 | N | 4, | 128–129 |
| 25 | CH3 | 1 | CH | 4, | 122–123 |
| 26 | F | 2 | N | 2,4, | 118–119 |
| 27 | F | 2 | CH | 2,4, | 144–145 |
| 28 | F | 2 | N | 3,4, | 119–121 |
| 29 | F | 2 | CH | 3,4, | 103–105 |
| 30 | CN | 1 | N | 4, | 115–116 |
| 31 | CN | 1 | CH | 4, | 103–104 |
| 32 | F,Cl | 2 | N | 2(F),4(Cl) | 125–127 |
| 33 | F,Cl | 2 | CH | 2(F),4(Cl) | 141–143 |
| 34 | F | 5 | N | 2,3,4,5,6, | 118–120 |
| 35 | CF3 | 1 | N | 4, | 102–103 |
| 36 | CF3 | 1 | CH | 4, | 91–92 |

The infrared spectrum of each compound in the above Table 1 is shown in attached FIGS. 1 to 36, respectively.

A derivative of oxirane represented by the formula (II), which is the starting material of the reaction, is prepared by reacting a ketone represented by the formula (IV):

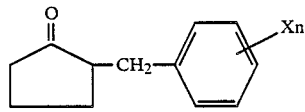
(IV)

wherein X and n have the same meanings as in the formula (I), with, for example, dimethyloxosulfonium methylide or dimethylsulfonium methylide in the presence of a diluent.

An example of the compound represented by the formula (IV) is 2-substituted benzylcyclopentanone. It can be prepared from 2-alkoxycarbonylcyclopentanone and a corresponding substituted benzyl halide according to the process described in Org. Syn., 45, 7 (1965) and J. Chem. Soc., (1950), 325. It can also be prepared from a corresponding substituted benzylhalide and an enamine of cyclopentanone. (See J. Pharm. Sci., 68, 1501 (1979)).

The diluent used in the process of preparing the compound represented by the formula (I) includes hydrocarbons such as benzene, toluene, xylene and hexane; halogenated hydrocarbons such as methylene chloride, chloroform and carbon tetrachloride; alcohols such as methanol and ethanol; ethers such as diethyl ether, diisopropyl ether and tetrahydrofuran; and other compounds such as acetonitrile, acetone, dimethylformamide and dimethylsulfoxide.

The process of the present invention may be carried out in the presence of the above-mentioned diluent together with a base. As examples of the base, alkali metal carbonates such as sodium carbonate and potassium carbonate; alkali metal hydroxide such as sodium hydroxide and potassium hydroxide; alkali metal alcoholates such as sodium methylate, sodium ethylate and potassium t-butylate; alkali metal hydrides such as sodium hydride and potassium hydride; and triethylamine and pyridine may be mentioned.

The process of the present invention is carried out in the following manner. An azole represented by the formula (III) is dissolved in a diluent exemplified above, and to the resulting solution is added an oxirane represented by the formula (II) in an amount of 0.5 to 1.0 equivalent. The solution may contain a base exemplified above, if necessary. Alternatively, the oxirane can be dissolved in the diluent first and to the resulting solution can be added an alkali metal salt of the azole.

The reaction temperature ranges from the freezing point to the boiling point of the above-mentioned diluent, but the preferred reaction temperature is from 0° C. to 100° C. The reaction time is from 1 hour to 3 hours. The reaction is preferably carried out with stirring.

After the reaction is completed, the reaction mixture is cooled and extracted with an organic solvent such as ethyl acetate, chloroform or benzene in iced water. The organic layer is separated, washed with water and dried. The solvent is distilled off under reduced pressure. The residues are purified to give the desired compound. Purification may be carried out by recrystallization or silica gel chromatography.

A derivative of azole (a derivative of azolylcyclopentanol) represented by the formula (I) exerts the following activities as an active ingredient of agricultural and horticultural composition.

(1) Fungicidal action on plant diseases

A derivative of azole of the present invention exerts the control effect on a wide variety of plant diseases listed below.

Rice plant: *Pyricularia oryzae, Cochliobolus miyabeanus, Xanthomonas oryzae, Rhizoctonia solani, Helminthosporium sigmoideum* and *Giberella fujikuroi.*

Apple tree: *Podosphaera leucotricha, Venturia inaequalis, Scherotinia mali, Alternaria mali* and *Valsa mali.*

Pear tree: *Alternaria kikuchiana, Phyllactinia pyri, Gymnosporangium haraeonum* and *Venturia nashicola.*

Grape-vine: *Unccinula necator* and *Phakospora ampelopsidis.*

Barley: *Erysiphe graminis* f. sp. *hordei, rhynchosporium secalis, Puccinia graminis* and *Puccinia triformis*.
Wheat: Puccinia recondita, Septoria tritici, Puccinia triformis and Erysiphe graminis f. sp. *tritici*.
Oriental melon plant: *Sphaerotheca fuliginea*.
Watermelon plant: *Fusarium oxysporum*.
Tomato plant: *Erysiphe cichoracearum* and *Alternaria solani*.
Eggplant: *Erysiphe cichoracearum*.
Strawberry plant: *Sephaerotheca humuli*.
Tobacco plant: *Erysiphe cichoracearum* and *Alternaria longipes*.
Sugar beat: *Cercospora beticola*.
Potato plant: *Alternaria solani*.
Soybean plant: *Cercospora kikuchii* and *Septoria glycines*.
Drupe fruits plant: *Sclerotinia cinerea*.
Other crop plants: *Botrytis cinerea* and *Sclerotinia sclerotiorum*.

A derivative of azole of the present invention produces not only the preventive effect but also the therapeutic effect on some of the above-mentioned plant diseases.

(2) Plant growth regulating effect

Recently, plant growth regulators have come into general use in agriculture and horticulture, as the mechanism governing the plant growth regulation by plant hormones has been elucidated. The usage of plant hormones includes, for example, the production of seedless grapes by means of gibberellin, the acceleration of rooting of cuttings by means of α-naphthaleneacetic acid and the growth retardation of wheat by means of 2-chloroethyltrimethylammonium chloride (trade name "CCC").

The utilization of techniques in controlling environment of plants applying plant growth regulators is now subjected not only to crops, vegetables and fruit trees but also to ornamental plant such as with flowers and further to wider range of plants such as trees. And there is an increasing possibility that the function of plant growth regulators is going to spread into rooting acceleration, flowering regulation, fruit bearing and thickening, growth acceleration, growth retarding and metabolism regulation. Plant growth regulators are increasing in their kinds and amount of consumption in recent years, but they are not so increasing as can be expected from the above possibilities.

The derivative of azole (derivative of azolylcyclopentanol) of the present invention produces the plant growth regulating effect (including herbicidal effect) on a wide variety of plants as shown below.
(1) Suppression of vegetative growth of plants, especially suppression of height growth.
(2) Increase of available nutrients in plants.
(3) Regulation of maturing stage or flowering time of plants.

The first activity mentioned above is useful for the suppression of weed growth (weed-killing function), the suppression of lawn, the prevention of lodging of rice plant and wheat, the suppression of height of soybean and cotton plants which make harvesting machine available, the suppression of axillary buds which promotes the growth of tobacco leaves, the suppression of hedge plant growth which reduces the frequency of pruning and the glowth retardation of ornamental plants which leads to an increased commercial value.

The second activity mentioned above contributes to the improvement of beet sugar, sugar cane, and citrus through the increase of sugar content and also to the improvement of crops and soybean through the increase of protein.

The third activity mentioned above makes is possible to ship fresh fruits and flowers at any time according to demands.

A derivative of azole represented by the formula (I) can be used as a fungicide, a plant growth regulator or a herbicide in the form of dust, wettable powder, granule, emulsifiable concentrate or solution with or without mixing a carrier (or diluent). It may also be used as such if necessary, namely, the formulation may contain, in addition to a carrier, adjuvants such as spreader, emulsifier, wetting agent, and sticking agent to ensure the effect.

Incidentally, the derivative of azole of the present invention can be used in the form of inorganic salt, organic salt or metal complex, because it container the 1,2,4-triazole ring or imidazole ring.

The derivative of azole of the present invention has an azolylmethyl group and a substituted benzyl group at the 1-position and 2-position, respectively, of the cyclopentane ring. Therefore, it should exist in the form of stereoisomers, e.g., geometrical isomer (cis form and trans form) and optical isomers. In this invention, the derivative of azole may be a single isomer or a mixture thereof at an arbitrary ratio. Thus, the agricultural and horticultural chemical pertaining to the present invention may contain one of the isomers or a mixture of the isomers as an active ingredient.

The present invention is now illustrated with the following examples which demonstrate the production of derivatives of azole and the effect of the agricultural and horticultural chemical containing a derivative of azole as an active ingredient.

EXAMPLE 1

Preparation of
2-(2,4-dichlorobenzyl)-1-(1H-imidazol-1-yl-methyl)cyclopentane-1-ol (Compound No. 8 in Table 1)

Into 20 ml of anhydrous dimethylformamide, 336 mg of sodium hydride (prepared by washing 60 % oily sodium hydride with dried benzene) were added while stirring under helium atmosphere, and after adding 950 mg of 1H-imidazol into the thus prepared mixture, the whole mixture was stirred at room temperature until bubbling was over. A solution of 1.8 g of 4-(2,4-dichlorobenzyl)-1-oxaspiro [2.4] heptane in 10 ml of anhydrous dimethylformamide was dropped into the thus obtained solution, and the whole mixture was stirred for 2 hours at 80° C.

After leaving the thus obtained reaction mixture to cool, it was poured into iced water, and the mixture wax extracted with ethyl acetate to obtain an organic layer. After washing the organic layer with water and drying the layer on anhydrous sodium sulfate, the solvent was distilled off from the layer under a reduced pressure to obtain a residue. By recrystallizing the residue with a mixture of hexane and ethyl acetate, 1.20 g of the compound shown in the above title was obtained.

The results of determination of the physical properties of the thus obtained compound are as follows and in addition, NMR spectrum of the compound was determined by using TMS as the internal standard and the results are shown by the following marks (the same marks are used in other Examples):
s: singlet d: doublet
m: multiplet
b: a broad line

Physical Properties (1) Melting point: 150°–151° C.

(2) Infrared absorption spectrum (KBr method): $\nu$max 3130, 2940, 1580, 1430 and 1100 cm$^{-1}$.

(3) NMR spectrum (DCDl$_3$, ppm): δ 1.38–1.97 (bs, 7 H), 2.50–3.18 (m, 2 H), 3.53 (bs, 1 H), 3,83 (d, 1H, J=14 Hz), 4.22 (d, 1 H, J=14 Hz), 7.03 (s, 2 H), 7.27–7.55 (m, 3 H) and 7.62 (s, 1 H).

EXAMPLE 2

Preparation of 2-(4-chlorobenzyl)-1-)1H-1,2,4,-triazol-1-yl-methyl)cyclopentane-1-ol (Compound No. 3 in Table 1)

Into 15 ml of anhydrous dimethylformamide, 1.0 g of 4-(4-chlorobenzyl)-10oxaspiro[2,4] heptane was added to be dissolved while stirring under a helium atmosphere, and into the thus prepared solution, 0.6 g of sodium salt of 1H-1,2,4-triazole of 90% in purity (commercial product, made by ALDRICH Co.) was slowly added. The mixture was stirred for 2 hours at 60° C.

After leaving the thus obtained reaction mixture to be cooled, the cooled reaction mixture was poured into water and the mixture was extracted with ethyl acetate to obtain an organic layer. After washing the layer with water and drying thereof an anhydrous sodium sulfate, the solvent was distilled off from the layer under a reduced pressure to obtain a residue.

By purifying the residue through silica gel column chromatography, 0.6 g of the compound of the above title was obtained, the physical properties thereof being shown as follows:

Physical Properties (1) Melting point: 115–116° C.

(2) Infrared absorption spectrum (KBr method): $\nu$max 3260, 2940, 1280, 1140 and 670 cm$^{-1}$ (3) NMR spectrum (CDCl$_3$, ppm): δ 1.35–2.13 (m, 7H), 2.48–2.77 (m, 2H), 3.02 (Bs, 1H 4.18 (s, 2H), 7.18 (d, 2H, J=9 Hz), 7.40 (d, 2H, J=9 Hz), 8.08 (s, 1H) and 8.25 (s, 1H).

The following two examples (Examples 3 and 4) are the examples of the preparation of a fungicide for use in agriculture and horticulture containing a derivative of azole according to the present invention as an active ingredient.

EXAMPLE 3

By pulverizing and mixing 3 parts by weight of one of the present compounds (Compound No. 5 in Table 1), 40 parts by weight of clay and 57 parts by weight of talc, a fungicide dust was prepared.

The thus prepared fungicide dust is used by scattering on the object.

EXAMPLE 4

By pulverizing and mixing 50 parts by weight of one of the present compounds (Compound No. 3 in Table 1), 5 parts by weight of a salt of ligninsulfonic acid, 3 parts by weight of a salt of an alkylsulfonic acid and 42 parts by weight of diatomaceous earth, a fungicide wettable powder was prepared.

The thus prepared fungicide wettable powder is used after diluting with water.

The following five examples (Examples 5 to 9) are the examples showing the fungicidal effect of the fungicide for use in agriculture and horticulture according to the present invention.

EXAMPLE 5

Pest control test against *Erysiphe graminis* f. sp. *tritici* on wheat

Onto the leaves of seadling of wheat (variety: NORIN No. 64, 16 seedlings per pot) at the second leaf stage cultured in an unglazed pot, a fungicide wettable powder prepared according to the method in Example 4 diluted with water to a predetermined concentration was sprayed at a rate of 5 ml/pot (control pot was sprayed with water only). After natural drying of the thus sprayed leaves, an aqueous suspension of the spores of *Erytsiphe graminis* f. sp *tritici* collected from the attacked leaves of wheat was sprayed onto the thus dried leaves of the potted wheat, and the thus treated seedlings were kept for 24 hours at temperature of from 20 to 25° C. in a highly humid atmosphere. Thereafter, the thus treated seedlings were left in a green house made of glass. AFter 10 days of the inoculation, the morbidity of the seeldings was examined on the basis of the following standard and the control value was calculated by the following formula from the average morbidity per leaf:

| Standard of the examination | |
|---|---|
| Morbidity index | Extent of disease infect |
| 0 | Not infected |
| 0.5 | A*$^1$ is less than 10%, |
| 1 | A is from 10 to less than 20%, |
| 2 | A is from 20 to less than 40%, |
| 3 | A is from 40 to less than 60%, |
| 4 | A is from 60 to less than 80%, and |
| 5 | A is larger than 80%. |

Note *$^1$A is the area rate of disease infect on the surface of the inoculated leaf.

$$\text{Control value} = \left(1 - \frac{\text{morbidity on treated pot}}{\text{morbidity on control pot}}\right) \times 100$$

The results are shown in Table 2.

TABLE 2

| Compound number (as in Table 1) | Concentration of the sprayed liquid (ppm) | Control value (%) |
|---|---|---|
| 1 | 125 | 100 |
| 2 | 125 | 100 |
| 3 | 125 | 100 |
| 4 | 125 | 100 |
| 5 | 125 | 100 |
| 6 | 125 | 100 |
| 7 | 125 | 100 |
| 8 | 125 | 100 |
| 9 | 125 | 95 |
| 10 | 125 | 90 |
| 11 | 125 | 95 |
| 12 | 125 | 95 |
| 13 | 125 | 100 |
| 14 | 125 | 100 |
| 15 | 125 | 100 |
| 16 | 125 | 100 |
| 17 | 125 | 100 |
| 18 | 125 | 100 |
| 19 | 125 | 100 |
| 20 | 125 | 100 |
| 21 | 125 | 50 |
| 22 | 125 | 65 |
| 23 | 125 | 70 |
| 24 | 125 | 75 |
| 25 | 125 | 70 |

TABLE 2-continued

| Compound number (as in Table 1) | Concentration of the sprayed liquid (ppm) | Control value (%) |
| --- | --- | --- |
| 26 | 125 | 100 |
| 27 | 125 | 68 |
| 28 | 125 | 100 |
| 29 | 125 | 100 |
| 30 | 125 | 100 |
| 31 | 125 | 62 |
| 32 | 125 | 100 |
| 33 | 125 | 75 |
| 34 | 125 | 100 |
| 35 | 125 | 100 |
| 36 | 125 | 100 |
| Triadimefon*¹ | 125 | 100 |
| Control | — | 0 |

Note:
*¹:Triadimefon is a commercial fungicide of the following compound as the active ingredient.

[Structural formula of Triadimefon]

EXAMPLE 6

Pest control test against *Sphaerotheca fuliginea* on cucumber plant

Onto the leave of seedling of cucumber (variety: SAGAMI-HAMPAKU, one seedling per pot, 3 pots in a test of one compound) at the second leaf stage cultured in an unglazed pot of 10 cm in diameter, a fungicide wettable powder prepared according to the method in Exampel 4 diluted with water to a predetermined concentration was sprayed at a rate of 5 ml/pot (control pot was sprayed with water only), and then the spores of *Sphaerotheca fuliginea* of cucumber were scattered onto the thus sprayed leave from the contracted leaf of cucumber plant by using a brush to inoculate on the leave, and the thus treated pots were left in a glass green house. After 7 days of the inoculation, the morbidity of the leaf of seedlings (one leaf/pot, three pots/compound) was examined according to the following standard, and the control value was calculated from the average morbidity per leaf while utilizing the same formula as in Example 5:

| Standard of the examination: | |
| --- | --- |
| Morbidity index | Extent of disease infect |
| 0 | Not infected |
| 0.5 | A*¹ is less than 10%, |
| 1 | A is from 10 to less than 20%, |
| 2 | A is from 20 to less than 40%, |
| 3 | A is from 40 to less than 60%, |
| 4 | A is from 60 to less than 80%, and |
| 5 | A is larger than 80%. |

Note *¹A is the area rate of disease infect on the surface of the inoculated leaf.

The results are shown in Table 3.

TABLE 3

| Compound number (as in Table 1) | Concentration of the sprayed liquid (ppm) | Control value (%) |
| --- | --- | --- |
| 1 | 62.5 | 100 |
| 2 | 62.5 | 100 |
| 3 | 62.5 | 100 |
| 4 | 62.5 | 100 |
| 5 | 62.5 | 100 |
| 6 | 62.5 | 100 |
| 7 | 62.5 | 100 |
| 8 | 62.5 | 95 |
| 9 | 62.5 | 98 |
| 10 | 62.5 | 70 |
| 11 | 62.5 | 100 |
| 12 | 62.5 | 90 |
| 13 | 62.5 | 100 |
| 14 | 62.5 | 60 |
| 15 | 62.5 | 100 |
| 16 | 62.5 | 100 |
| A commercial fungicide *¹ | 125 | 100 |
| Control | — | 0 |

Note:
*¹: A fungicide of quinoxaline series represented by the following formula:

[Structural formula of quinoxaline fungicide]

EXAMPLE 7

Pest control test against *Puccinia recondita* f. sp. *tritici* on wheat

Onto the leave of seedling of wheat (variety: NORIN No. 64, 16 seedlings per pot) at the second leaf stage cultured in an unglazed pot of 10 cm in diameter, a fungicide wettable powder prepared according to the method in Example 4 diluted with water at a predetermined concentration was sprayed at a rate of 5 ml/pot (control pot was sprayed with water only). After natural drying of the thus sprayed leave, an aqueous suspension of the uredospores of *Puccinia recondita* f. sp. *tritici* collected from the attacked leaves of wheat was sprayed onto the thus dried leaves of the potted wheat, and the thus treated seedlings were kept for 24 hours at a temperature of from 20° to 25° C. in a highly humid atmosphere. Thereafter, the thus treated seedlings were left in a glass green house, and after 7 days, the morbidity was examined on the basis of the following standard. The control value of each of the fungicide was calculated by the formula shown in Example 5 from the average morbidity per leaf of the 10 seedlings per pot:

Standards of the examination:
The same as in Example 6.
The results are shown in Table 4.

TABLE 4

| Compound number (as in Table 1) | Concentration of the sprayed liquid (ppm) | Preventive value (%) |
| --- | --- | --- |
| 1 | 200 | 100 |
| 2 | 200 | 100 |
| 3 | 200 | 100 |
| 4 | 200 | 100 |
| 5 | 200 | 100 |
| 6 | 200 | 100 |
| 7 | 200 | 100 |
| 8 | 200 | 100 |
| 9 | 200 | 78 |
| 10 | 200 | 95 |
| 11 | 200 | 73 |
| 12 | 200 | 88 |
| 13 | 200 | 50 |
| 14 | 200 | 75 |
| 15 | 200 | 45 |

TABLE 4-continued

| Compound number (as in Table 1) | Concentration of the sprayed liquid (ppm) | Preventive value (%) |
| --- | --- | --- |
| 16 | 200 | 80 |
| 17 | 200 | 90 |
| 18 | 200 | 75 |
| 19 | 200 | 68 |
| 20 | 200 | 100 |
| 21 | 200 | 65 |
| 22 | 200 | 45 |
| 23 | 200 | 75 |
| 24 | 200 | 75 |
| 25 | 200 | 83 |
| 26 | 200 | 88 |
| 27 | 200 | 65 |
| 28 | 200 | 100 |
| 29 | 200 | 100 |
| 30 | 200 | 88 |
| 31 | 200 | 68 |
| 32 | 200 | 100 |
| 33 | 200 | 70 |
| 34 | 200 | 85 |
| Triadimefon | 200 | 100 |
| Control | — | 0 |

EXAMPLE 8

Pest control test against *Cochliobolus miyabeanus* on rice plant

In the unglazed pots of 10 cm in diameter, the seeds of rice plant (variety: SASANISHIKI) were sown at a rate of 16 seeds/pot, and at the stage of 4 to 5 leaves, the fungicide wettable powder prepared according to the method in Example 4 was diluted with water to a predetermined concentration, and the thus prepared aqueous suspension of the fungicide was sprayed onto the seedlings of rice plant at a rate of 5 ml/pot. After natural drying the thus treated leaves of the rice seedlings, an aqueous suspension of the spores of *Cochliobolus miyabeanus* (at a concentration of 15 spores in the visual field of a microscope of 150 magnification) preliminarily cultured was sprayed onto the leaves of seedlings at a rate of 5 ml/pot for inoculation. After inoculation, the pots were immediately taken into an inoculation room of 25° C. and of saturated humidity, and after keeping thereof for 2 days, the pots were moved into a glass green house to be attacked. At the fifth day after the inoculation, the number of the disease spots on 10 leaves per pot was enumerated, and the control value of each of the fungicides was calculated according to the following formula:

Control value (%) = $(1 - A/b) \times 100$ wherein A is the number of disease spots in the treated pots and B is that in the control pots (not being sprayed with the fungicide).

The results are shown in Table 5.

TABLE 5

| Compound number (as in Table 1) | Concentration of the sprayed liquid (ppm) | Preventive value (%) |
| --- | --- | --- |
| 1 | 300 | 100 |
| 2 | 300 | 100 |
| 3 | 300 | 100 |
| 4 | 300 | 100 |
| 5 | 300 | 100 |
| 6 | 300 | 100 |
| 7 | 300 | 92 |
| 8 | 300 | 100 |
| 9 | 300 | 100 |
| 10 | 300 | 100 |
| 11 | 300 | 99 |
| 12 | 300 | 98 |
| 13 | 300 | 99 |
| 14 | 300 | 98 |
| 15 | 300 | 100 |
| 16 | 300 | 100 |
| 17 | 300 | 80 |
| 18 | 300 | 95 |
| 19 | 300 | 98 |
| 20 | 300 | 97 |
| 21 | 300 | 100 |
| 22 | 300 | 90 |
| 23 | 300 | 99 |
| 24 | 300 | 100 |
| 25 | 300 | 100 |
| 26 | 300 | 100 |
| 27 | 300 | 100 |
| 28 | 300 | 100 |
| 29 | 300 | 100 |
| 30 | 300 | 100 |
| 31 | 300 | 98 |
| 32 | 300 | 100 |
| 33 | 300 | 100 |
| 34 | 300 | 100 |
| EDDP*[1] | 300 | 88 |
| Control | — | 0 |

Note:
*[1]: A commercial fungicide containing the following compound as an active ingredient:

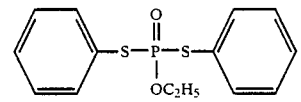

EXAMPLE 9

In vitro test against several fungal species

Antifungal properties of the present compounds against several fungal species were examined as follows.

After thoroughly mixing each of the present compounds with the PSA culture medium at a prescribed concentration, the thus prepared mixture was poured into dishes of 9 cm in diameter in an amount of 10 ml per dish to prepare plate culture medium. On the other hand, each of the fungal species cultured in a plate culture medium was punched by a cork borer of 6 mm in diameter and inoculated on the thus prepared plate culture medium in the dishes. After inoculating, each of the thus inoculated fungi was cultured for from one to three days at a temperature suitable for each fungus, and the growth of the fungus was determined by the diameter of each fungal colony. The results were compared to the result on the control (the culture medium not containing any fungicide), and on the basis of the following formula, the rate of control of the mycelial growth was obtained:

$R = (d_c - d_t)(100/d_c)$ wherein R represents the rate of control of the mycelial growth of a fungus, $d_t$ represents the diameter of the fungal colony on the culture medium plate containing each of the present compound and $d_c$ represents the diameter of the fungal colony on the culture medium plate not containing any fungicide (control).

The thus obtained results were evaluated on the basis of the following standard into 5 ranks and are shown in Table 6.

| Standard for evaluation: | |
|---|---|
| Index of growth control | Rate of control of mycelial growth |
| 5 | from 100 to 90% |
| 4 | from 89 to 70% |
| 3 | from 69 to 40% |
| 2 | from 39 to 20% |
| 1 | less than 20% |

TABLE 6

| Compound number (as in Table 1) | Concentration of the sprayed liquid (μg/ml) | \multicolumn{10}{c}{Fungal species tested (refer to Note)} | | | | | | | | | |
|---|---|---|---|---|---|---|---|---|---|---|---|
| | | P.o. | C.m. | R.s. | G.f. | He.s. | Bo.c. | F.n. | S.c. | A.k. | V.m. |
| 1 | 100 | 5 | 5 | 3 | 5 | 4 | 5 | 5 | 5 | 5 | 5 |
| 2 | 100 | 5 | 5 | 3 | 5 | 3 | 3 | 2 | 5 | 4 | 4 |
| 3 | 100 | 5 | 5 | 3 | 5 | 5 | 5 | 5 | 5 | 5 | 5 |
| 4 | 100 | 5 | 5 | 3 | 5 | 5 | 5 | 4 | 5 | 5 | 5 |
| 5 | 100 | 5 | 5 | 3 | 5 | 4 | 5 | 5 | 5 | 5 | 5 |
| 6 | 100 | 5 | 5 | 3 | 5 | 3 | 4 | 2 | 5 | 5 | 5 |
| 7 | 100 | 5 | 5 | 5 | 5 | 5 | 5 | 5 | 5 | 4 | 5 |
| 8 | 100 | 5 | 5 | 4 | 5 | 4 | 4 | 5 | 5 | 4 | 5 |
| 9 | 100 | 5 | 5 | 2 | 5 | 4 | 2 | 4 | 5 | 3 | 5 |
| 10 | 100 | 5 | 5 | 4 | 5 | 4 | 3 | 5 | 5 | 4 | 5 |
| 11 | 100 | 4 | 5 | 3 | 5 | 4 | 4 | 4 | 5 | 3 | 5 |
| 12 | 100 | 5 | 5 | 3 | 5 | 4 | 3 | 5 | 5 | 3 | 5 |
| 13 | 100 | 4 | 5 | 3 | 4 | 4 | 3 | 5 | 5 | 3 | 5 |
| 14 | 100 | 5 | 5 | 3 | 5 | 4 | 3 | 4 | 5 | 3 | 5 |
| 15 | 100 | 4 | 5 | 3 | 5 | 5 | 5 | 4 | 5 | 3 | 5 |
| 16 | 100 | 5 | 5 | 4 | 5 | 5 | 4 | 5 | 5 | 4 | 5 |
| 17 | 100 | 5 | 5 | 2 | 5 | 4 | 4 | 4 | 5 | 4 | 5 |
| 18 | 100 | 5 | 5 | 3 | 5 | 4 | 4 | 4 | 5 | 3 | 5 |
| 19 | 100 | 5 | 5 | 3 | 4 | 4 | 2 | 3 | 5 | 3 | 5 |
| 20 | 100 | 5 | 5 | 3 | 5 | 5 | 5 | 5 | 5 | 5 | 5 |
| 21 | 100 | 5 | 5 | 4 | 5 | 5 | 5 | 5 | 5 | 5 | 5 |
| 22 | 100 | 4 | 5 | 2 | 4 | 4 | 4 | 4 | 5 | 3 | 4 |
| 23 | 100 | 5 | 5 | 3 | 5 | 4 | 3 | 4 | 5 | 3 | 5 |
| 24 | 100 | 5 | 5 | 3 | 5 | 5 | 5 | 5 | 5 | 5 | 5 |
| 25 | 100 | 5 | 5 | 3 | 5 | 5 | 4 | 4 | 5 | 5 | 5 |
| 26 | 100 | 4 | 5 | 2 | 5 | 4 | 5 | 4 | 5 | 4 | 5 |
| 27 | 100 | 5 | 5 | 3 | 5 | 4 | 4 | 5 | 5 | 4 | 5 |
| 28 | 100 | 5 | 5 | 5 | 5 | 5 | 5 | 5 | 5 | 5 | 5 |
| 29 | 100 | 5 | 5 | 4 | 5 | 5 | 4 | 4 | 5 | 4 | 5 |
| 30 | 100 | 5 | 4 | 1 | 5 | 3 | 4 | 4 | 5 | 3 | 5 |
| 31 | 100 | 5 | 5 | 2 | 4 | 3 | 3 | 2 | 5 | 3 | 5 |
| 32 | 100 | 5 | 5 | 3 | 5 | 5 | 5 | 5 | 5 | 4 | 5 |
| 33 | 100 | 5 | 5 | 3 | 5 | 4 | 4 | 5 | 5 | 4 | 5 |
| 34 | 100 | 5 | 5 | 3 | 5 | 5 | 5 | 3 | 5 | 3 | 5 |

Note:
The abbreviation in TABLE 6 indicate the fungal species as follows:
P.o.: *Pyricularia oryzae* on rice plant
C.m.: *Cochliobolus miyabeanus* on rice plant
R.s.: *Rhizoctonia solani* on rice plant
G.f.: *Gibberella fujikuroi* on rice plant
He.s.: *Helminthosporium sigmoideum* on rice plant
Bo.c.: *Botyrtis cinerea*
F.n.: *Fusarium oxysporum* f. *niveum* on water-melon
S.c.: *Sclerotinia cinerea* on peach tree
A.k.: *Alternaria kikuchiana* on pear tree
V.m.: *Valsa mali* on apple tree

EXAMPLE 10

Preparation of plant growth regulator composition and herbicide composition containing a derivative of azole as an active ingredient.

(1) Wettable Powder
The following components were pulverized and mixed to prepare a wettable powder, which would be applied after dilution with water.

| Compound of the invention (compound No. 3 in Table 1) | 50 parts by weight |
|---|---|
| Lignin sulfonate | 5 parts by weight |
| Alkyl sulfonate | 3 parts by weight |
| Diatomaceous earth | 42 parts by weight |

(2) Emulsifiable concentrate
The following components were uniformly mixed to prepare an emulsifiable concentrate, which would be applied after dilution with water.

| Compound of this invention (compound No. 20 in Table 1) | 25 parts by weight |
|---|---|
| Xylene | 65 parts by weight |
| Polyoxyethylene alkylaryl ether | 10 parts by weight |

(3) Granule
The following components were uniformly mixed together with water and the mixture was granulated by an extrusion granulator, followed by drying.

| Compound of this invention (compound No. 11 in Table 1) | 8 parts by weight |
|---|---|
| Bentonite | 40 parts by weight |
| Clay | 45 parts by weight |
| Lignin sulfonate | 7 parts by weight |

EXAMPLE 11

Plant length inhibition for wheat

Ten wheat grains were sown in a glass petri dish 8.5 cm in diameter, containing 5 ml of 50 ppm solution of the compound under test. (The variety of wheat is AOBA No. 3). After growing indoors at 27° C. for 7 days, the plant length was measured. The results are shown in Table 7.

It is noted from Table 7 that all the compounds tested produced a pronounced effect of inhibiting the growth of plant length, particularly in the case of triazole-type compounds. No phytotoxicity was observed.

TABLE 7

| Compound number (as in Table 1) | Inhibition of plant length (%) | Phytotoxicity |
| --- | --- | --- |
| 1 | 82.8 | None |
| 2 | 54.1 | None |
| 3 | 88.5 | None |
| 4 | 42.6 | None |
| 5 | 81.8 | None |
| 6 | 46.7 | None |
| 7 | 85.6 | None |
| 8 | 43.5 | None |
| 9 | 3.8 | None |
| 10 | 3.1 | None |
| 11 | 13.7 | None |
| 12 | 3.5 | None |
| 13 | 20.4 | None |
| 14 | 35.7 | None |
| 15 | 7.2 | None |
| 16 | 11.9 | None |
| 17 | 45.6 | None |
| 18 | 81.8 | None |
| 19 | 16.5 | None |
| 20 | 63.4 | None |
| 21 | 3.7 | None |
| 22 | 54.1 | None |
| 23 | 15.2 | None |
| 24 | 85.4 | None |
| 25 | 38.1 | None |
| 26 | 15.8 | None |
| 27 | 11.8 | None |
| 28 | 62.6 | None |
| 29 | 19.6 | None |
| 30 | 46.6 | None |
| 31 | 11.2 | None |
| 32 | 79.0 | None |
| 33 | 14.7 | None |
| 34 | 72.5 | None |
| 35 | 35.5 | None |
| 36 | 14.3 | None |

Average length of wheat in the control group was 80.5 mm.

EXAMPLE 12

Weeds Killing Test (soil treatment before germination)

Several kinds of weed seeds were sown in sandy loam filled in a planter (650×210×220 mm). On the day subsequent to sowing, the soil surface was sprayed with a properly diluted liquid of the emulsifiable concentrate prepared according to the method in Example 10 (2).

The weeds were grown in a greenhouse made of glass, and the weeding effect was observed on 21st day after treatment. The weeding effect was rated according to the following standard.

The results are shown in Table 8.

| Index | Rate of Killing |
| --- | --- |
| 0 | No weeding effect |
| 1 | Weeding effect of 30% |
| 2 | Weeding effect of 31 to 50% |
| 3 | Weeding effect of 51 to 70% |
| 4 | Weeding effect of 71 to 90% |
| 5 | Weeding effect of 91 to 100% |

TABLE 8

| Compound number (as in Table 1) | Weeds tested (Refer to Note) | | | | |
| --- | --- | --- | --- | --- | --- |
| | A.r. | B.p. | S.n. | E.f. | S.v. |
| 1 | 5 | 5 | 5 | 5 | 5 |
| 2 | 4 | 5 | 5 | 5 | 5 |
| 3 | 5 | 5 | 5 | 5 | 5 |
| 4 | 4 | 5 | 5 | 4 | 4 |
| 5 | 5 | 5 | 5 | 5 | 5 |
| 6 | 5 | 4 | 5 | 4 | 4 |
| 7 | 5 | 5 | 5 | 5 | 5 |
| 8 | 5 | 4 | 5 | 4 | 5 |
| 9 | 4 | 4 | 4 | 3 | 3 |
| 10 | 4 | 4 | 4 | 3 | 3 |
| 11 | 5 | 5 | 5 | 4 | 4 |
| 13 | 5 | 5 | 5 | 5 | 4 |
| 14 | 5 | 5 | 5 | 5 | 5 |
| 15 | 5 | 5 | 5 | 4 | 4 |
| 16 | 5 | 5 | 5 | 4 | 4 |
| 17 | 5 | 5 | 5 | 5 | 5 |
| 18 | 5 | 5 | 5 | 5 | 5 |
| 19 | 5 | 5 | 5 | 5 | 5 |
| 20 | 5 | 5 | 5 | 5 | 5 |
| 21 | 5 | 5 | 5 | 4 | 4 |
| 22 | 5 | 5 | 5 | 5 | 5 |
| 23 | 5 | 5 | 5 | 5 | 5 |
| 24 | 5 | 5 | 5 | 5 | 5 |
| 25 | 5 | 5 | 5 | 5 | 5 |
| 26 | 5 | 5 | 5 | 5 | 5 |
| 27 | 5 | 5 | 5 | 5 | 5 |
| 28 | 5 | 5 | 5 | 5 | 5 |
| 29 | 5 | 5 | 5 | 5 | 5 |
| 30 | 5 | 5 | 5 | 4 | 4 |
| 31 | 5 | 5 | 5 | 5 | 5 |
| 32 | 5 | 5 | 5 | 5 | 5 |
| 33 | 5 | 5 | 5 | 5 | 5 |
| 34 | 5 | 5 | 5 | 5 | 5 |
| 35 | 5 | 5 | 5 | 5 | 5 |
| 35 | 5 | 5 | 5 | 5 | 5 |
| Control | 0 | 0 | 0 | 0 | 0 |

Note:
The abbreviations in TABLE 8 indicate the weeds as follows:
A.r.: *Amaranthus retyoflexus*
B.p.: *Bidens pilosa*
S.n.: *Solanum nigrum*
E.f.: *Echinochloa frumentaceum*
S.v.: *Setaria viridis*

What is claimed is:

1. A derivative of azole represented by the formula (I):

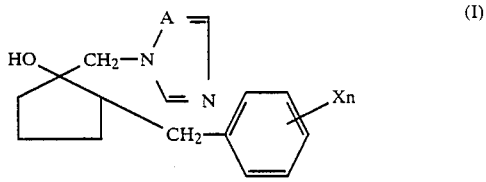

wherein X represents a hydrogen atom, a halogen atom, an alkyl group having 1 to 5 carbon atoms, a trihalomethyl group, a phenyl group, a cyano group or a nitro group and X can be the same or different group or atom, n represents an integer of 1, 2 or 5 when X is a fluorine atom and 1 or 2 when X is not a fluorine atom, and A represents a nitrogen atom.

2. A derivative of azole according to claim 1, wherein said X represents a hydrogen atom, a chlorine atom, a fluroine atom, a bromine atom, a nitro group, a methyl group, a t-butyl group, a phenyl group or a trifluoromethyl group, said n represents 1, 2 or 5 when X is a fluroine atom and 1 or 2 when X is not a fluorine atom and said A represents a nitrogen atom.

3. A derivative of azole according to claim 1, wherein said X represents a hydrogen atom, a 4-chlorine atom, a 4-fluorine atom, a 4-bromine atom or a 4-methyl group, said n is 1 and said A is a nitrogen atom.

4. A derivative of azole according to claim 1, wherein said X represents 2,4-chlorine atoms, 3,4-fluorine atoms, 2,4-fluorine atoms or 2-fluorine,4-chlorine atoms, and n is 2 and said A is a nitrogen atom.

5. A derivative of azole according to claim 1, wherein said X represents a fluorine atom, said n is 5 and said A is a nitrogen atom.

6. A derivative of azole according to claim 3, wherein said X is a 4-chlorine atom.

7. An agricultural and horticultural composition having a fungicidal activity, a plant growth regulating activity or a herbicidal activity, consisting essentially of a derivative of azole represented by the formula (I):

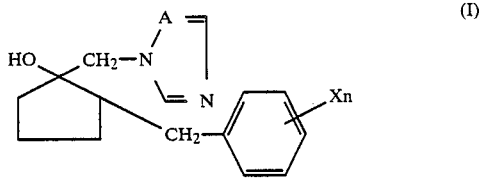

wherein X represents a hydrogen atom, a halogen atom, an alkyl group having 1 to 5 carbon atoms, a trihalomethyl group, a phenyl group, a cyano group or a nitro group and X can be the same or different group or atom, n is selected from the group of 1, 2 and 5 when x is a fluorine atom and selected from the group of 1 and 2 when X is not a fluorine atom, and A represents a nitrogen atom, in an amount effective as a fungicide, a plant growth regulator, or a herbicide and an agriculturally and horticulturally acceptable carrier.

8. An agricultural and horticultural composition according to claim 7, wherein said X represents a hydrogen atom, a chlorine atom, a fluorine atom, a bromine atom, a cyano group, a nitro group, a methyl group, a t-butyl group, a pnehyl group or a trifluoromethyl group, n is selected from the group of 1,2 and 5 when X is a fluorine atom and selected from the group of 1 and 2 when X is not a fluorine atom, and A represents a nitrogen atom.

9. An agricultural and horticultural composition of claim 7 having a fungicidal activity, wherein X represents a 4-chlorine atom, a 4-fluorine atom, a 4-bromine atom, a 4-methyl group, a 4-t-butyl group or a 4-phenyl group, n is 1 and A is a nitrogen atom.

10. An agricultural and horticultural composition of claim 7 having a fungicidal activity, wherein X represents 2,4-chlorine atoms, 2,4-fluorine atoms, 3,4-fluorine atoms or 2-fluorine, 4-chlorine atoms, n is 2 and A is a nitrogen atom.

11. An agricultural and horticultural composition of claim 7 having a plant growth regulating activity, wherein X represents a 4-chlorine atom, a 4-fluorine atom, a 4-bromine atom, a 2-chlorine atom, a 4-methyl group or a 4-cyano group, n is 1 and A is a nitrogen atom.

12. An agricultural and horticultural composition of claim 7 having a plant growth regulating activity, wherein X represents 2,4-chlorine atoms, 2,6-fluorine atoms, 3,4-fluorine atoms or 2-fluorine,4-chlorine atoms, n is 2 and A is a nitrogen atom.

13. An agricultural and horticultural composition of claim 7 having a herbicidal activity, wherein X represents a 4-chlorine atom, a f-fluorine atom, a 4-bromine atom or a 4-methyl group, n is 1 and A is a nitrogen atom.

14. An agricultural and horticultural composition of claim 7 having a herbicidal activity, wherein X represents 2,4-chlorine atoms, 2,4-fluorine atoms or 2-fluorine,4-chlorine atoms, n is 2 and A is a nitrogen atom.

* * * * *

UNITED STATES PATENT AND TRADEMARK OFFICE
CERTIFICATE OF CORRECTION

PATENT NO. : 4,863,505

DATED : September 5, 1989

INVENTOR(S) : Satoru Kumazawa, et al.

It is certified that error appears in the above-identified patent and that said Letters Patent is hereby corrected as shown below:

Column 17, line 15, change "and n" to --said n--.

Column 18, line 35, change "f-fluorine" to --4-fluorine--.

Column 18, line 7, change "pnehyl" to --phenyl--.

Signed and Sealed this

Fifteenth Day of October, 1991

Attest:

HARRY F. MANBECK, JR.

*Attesting Officer*　　　　　*Commissioner of Patents and Trademarks*